US00PP19315P2

(12) United States Plant Patent
Schoorl

(10) Patent No.: US PP19,315 P2
(45) Date of Patent: Oct. 14, 2008

(54) ***CELOSIA* PLANT NAMED 'VENEZUELA PINK'**

(50) Latin Name: *Celosia argentea*
Varietal Denomination: Venezuela Pink

(75) Inventor: Paul Schoorl, Rijsenhout (NL)

(73) Assignee: Helga Fehmel-Fleisher, Achern (DE)

( * ) Notice: Subject to any disclaimer, the term of this patent is extended or adjusted under 35 U.S.C. 154(b) by 0 days.

(21) Appl. No.: 11/881,791

(22) Filed: Jul. 27, 2007

(51) Int. Cl.
*A01H 5/00* (2006.01)

(52) U.S. Cl. ..... Plt./263.1
(58) Field of Classification Search ..... Plt./263.1
See application file for complete search history.

(56) References Cited

PUBLICATIONS

Upov–rom Plant Variety Database 2007/06 GTI Jouve Retrieval Software, Citation for Celosia 'Venezuela Pink' one page.*

* cited by examiner

*Primary Examiner*—Kent L. Bell
*Assistant Examiner*—June Hwu
(74) *Attorney, Agent, or Firm*—C. A. Whealy

(57) ABSTRACT

A new and distinct cultivar of *Celosia* plant named 'Venezuela Pink', characterized by its upright and compact plant habit; freely branching habit; freely flowering habit; light purple-colored flowers arranged on dense compound spikes; and good garden performance.

2 Drawing Sheets

Botanical designation: *Celosia argentea.*
Cultivar denomination: 'VENEZUELA PINK'.

BACKGROUND OF THE INVENTION

The present invention relates to a new and distinct cultivar of *Celosia,* botanically known as *Celosia argentea* and hereinafter referred to by the name 'Venezuela Pink'.

The new *Celosia* is a naturally-occurring whole plant mutation of the *Celosia argentea* cultivar Venezuela Dark, not patented. The new *Celosia* was discovered and selected by the Inventor as a single flowering plant from within a population of plants of the cultivar Venezuela Dark in a greenhouse controlled environment in Rijsenhout, The Netherlands in 2004.

Asexual reproduction of the new *Celosia* by cuttings in a controlled environment in Rijsenhout, The Netherlands since 2004, has shown that the unique features of this new *Celosia* are stable and reproduced true to type in successive generations.

SUMMARY OF THE INVENTION

The cultivar Venezuela Pink has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Venezuela Pink'. These characteristics in combination distinguish 'Venezuela Pink' as a new and distinct cultivar of *Celosia:*

1. Upright and compact plant habit.
2. Freely branching habit.
3. Freely flowering habit.

4. Light purple-colored flowers arranged on dense compound spikes.
5. Good garden performance.

Plants of the new *Celosia* differ from plants of the parent, the cultivar Venezuela Dark, primarily in flower color as plants of the cultivar Venezuela Dark have darker colored flowers than plants of the new *Celosia.* In addition, plants of the new *Celosia* are more compact than and not as vigorous as plants of the cultivar Venezuela Dark.

Plants of the new *Celosia* can be compared to plants of the cultivar Zancelor, disclosed in a U.S. Plant patent application No. 11/881,792 filed concurrently. Plants of the new *Celosia* and the cultivar Zancelor differ primarily in inflorescence form and flower color.

BRIEF DESCRIPTION OF THE PHOTOGRAPHS

The accompanying colored photographs illustrate the overall appearance of the new *Celosia,* showing the colors as true as it is reasonably possible to obtain in colored reproductions of this type. Colors in the photographs may differ slightly from the color values cited in the detailed botanical description which accurately describe the colors of the new *Celosia.*

The photograph on the first sheet comprises a side perspective view of a typical flowering plant of 'Venezuela Pink' grown in a container.

The photograph on the second sheet is a close-up view of typical leaves and inflorescences of 'Venezuela Pink'.

DETAILED BOTANICAL DESCRIPTION

The aforementioned photograph and following observations, measurements and values describe plants grown during the autumn in Rijsenhout, The Netherlands in containers and under commercial practice in a glass-covered greenhouse with day and night temperatures ranging from 20° C. to 22° C. Plants were pinched one time. Plants had been growing for about four months when the photographs and description were taken. In the following description, color references are made to The Royal Horticultural Society Colour Chart, 2001 Edition, except where general terms of ordinary dictionary significance are used.

Botanical classification: *Celosia argentea* cultivar Venezuela Pink.

Parentage: Naturally-occurring whole plant mutation of *Celosia argentea* cultivar Venezuela Dark, not patented.

Propagation:

*Type.*—By cuttings.

*Time to initiate and develop roots.*—About 9 to 14 days.

*Root description.*—Fine, fibrous; greyed brown, 199D, in color.

*Rooting habit.*—Freely branching; dense.

Plant description:

*Plant form/habit.*—Herbaceous annual typically grown as a potted plant. Upright and compact plant habit; narrow inverted triangle. Freely branching habit; about five lateral branches per plant developed when pinched. Moderate to low vigor.

*Plant height.*—About 25 cm.

*Plant width* (*spread*).—About 18 cm.

*Lateral branches.*—Length: About 20 cm to 22 cm. Diameter: About 3 mm to 4 mm. Internode length: About 1 cm to 1.5 cm. Texture: Smooth, glabrous. Color: 138B overlain with 176C.

Foliage description:

*Arrangement.*—Alternate; simple.

*Length.*—About 6 cm to 10 cm.

*Width.*—About 2 cm to 4 cm.

*Shape.*—Elliptic to lanceolate.

*Apex.*—Acute.

*Base.*—Attenuate.

*Margin.*—Crenate to entire.

*Texture, upper and lower surfaces.*—Smooth, glabrous.

*Venation pattern.*—Pinnate.

*Color.*—Developing leaves, upper surface: Close to 137A. Developing leaves, lower surface: 139B. Fully expanded leaves, upper surface: 137A; random sectors and spots, 187A. venation, 154D. Fully expanded leaves, lower surface: 138A; venation, 199D.

*Petiole length.*—About 1 cm to 2.5 cm.

*Petiole diameter.*—About 2 mm.

*Petiole texture, upper and lower surfaces.*—Smooth, glabrous.

*Petiole color, upper surface.*—154D.

*Petiole color, lower surface.*—199D.

Flower description:

*Flower type/habit.*—Single tubular flowers arranged in terminal compound spikes; flowers face mostly upright. Freely flowering habit, about 800 to 1,000 flowers per inflorescence; inflorescences dense.

*Fragrance.*—None detected.

*Natural flowering season.*—Continuously flowering during the summer in The Netherlands. Flowers persistent.

*Postproduction longevity.*—Inflorescences last about two to three months on the plant.

*Inflorescence height.*—About 6 cm.

*Inflorescence diameter.*—About 5 cm.

*Flower diameter.*—About 2 mm.

*Flower depth.*—About 1.5 mm to 1.8 mm.

*Petals.*—None observed.

*Sepals.*—Quantity per flower: Typically five. Length: About 8 mm. Width: About 1 mm. Shape: Lanceolate. Apex: Acute. Margin: Entire. Texture, upper and lower surfaces: Smooth, glabrous. Color: When opening and fully opened, upper surface: 77B to 77C; color becoming closer to 77D with development. When opening and fully opened, lower surface: 77B to 77C; color becoming closer to 77D with development.

*Pedicels.*—Length: About 2 mm. Diameter: About 1 mm. Angle: About 45° from vertical. Strength: Weak; flexible. Texture: Smooth, glabrous. Color: 144C.

*Reproductive organs.*—Stamens: Quantity per flower: Typically five. Filament color: Closer to N81B. Anther shape: Elliptic. Anther length: About 1 mm. Anther color: Close to N81B. Pollen amount: Scarce. Pollen color: Close to 13A. Pistils: Quantity per flower: One. Stigma color: Close to 154D. Style length: About 9 mm. Style color: Close to N74B. Ovary color: Close to 165D.

*Seeds.*—Length: About 1.5 mm. Diameter: About 1.5 mm. Color: 202A.

Disease/pest resistance: Plants of the new *Celosia* have not been noted to be resistant to pathogens and pests common to *Celosia*.

Garden performance: Plants of the new *Celosia* have been observed to have good garden performance and tolerate rain, wind and temperatures ranging from about 5° C. to 35° C.

It is claimed:

1. A new and distinct *Celosia* plant named 'Venezuela Pink' as illustrated and described.

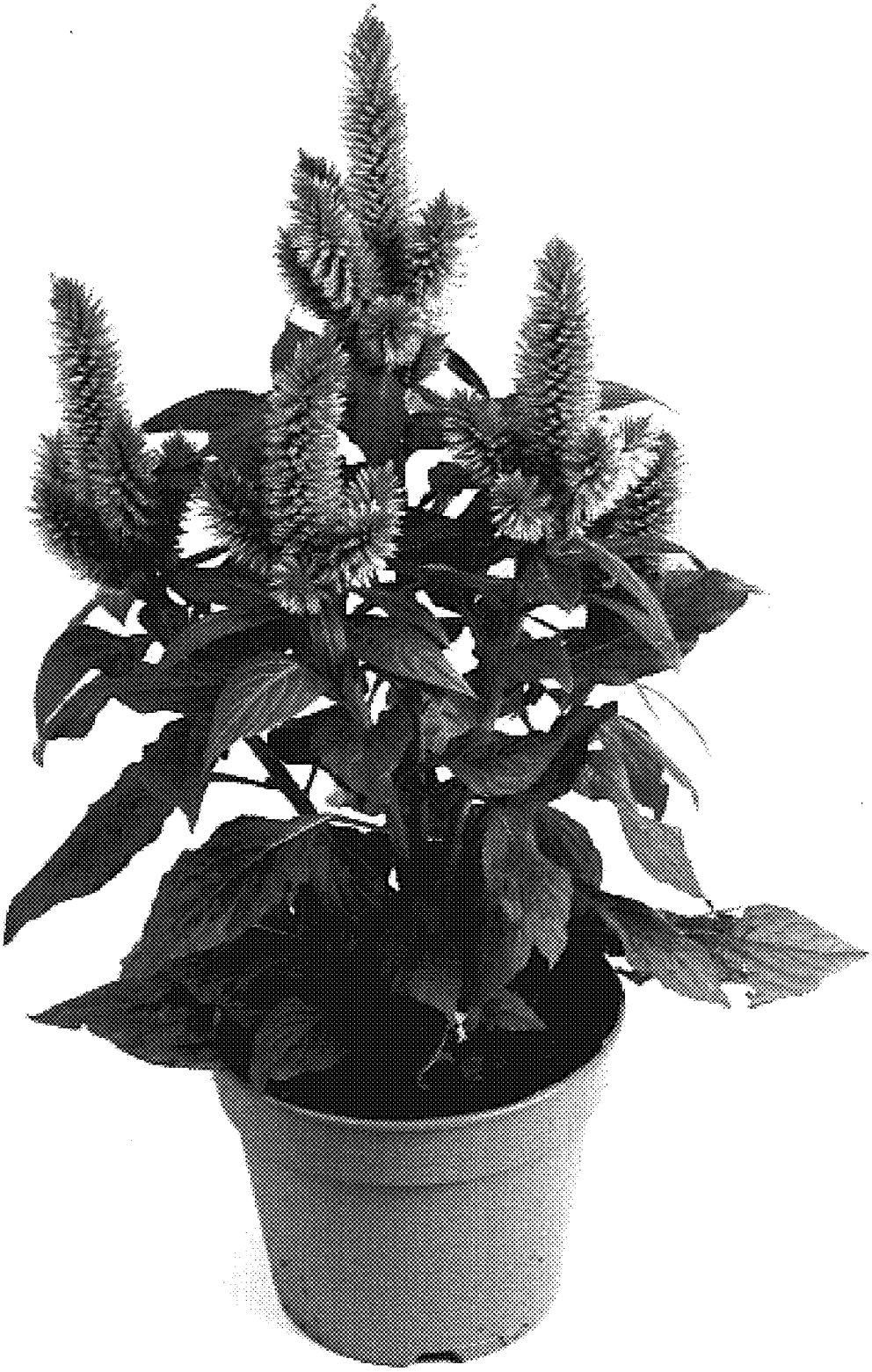

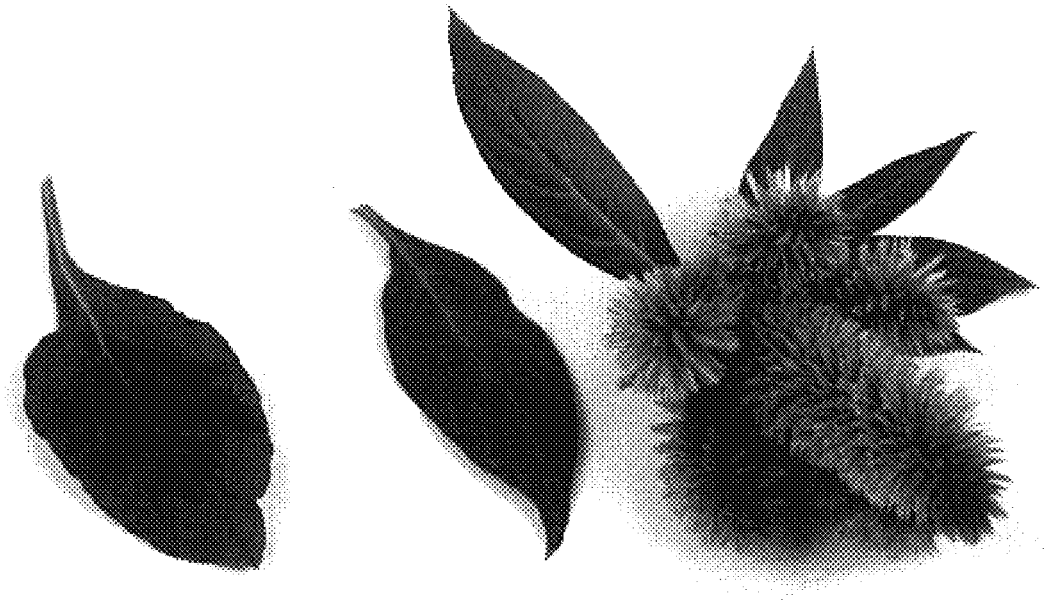

* * * * *